United States Patent

Mann

[11] Patent Number: 5,948,006
[45] Date of Patent: Sep. 7, 1999

[54] TRANSCUTANEOUS TRANSMISSION PATCH

[75] Inventor: Carla M. Mann, Beverly Hills, Calif.

[73] Assignee: Advanced Bionics Corporation, Sylmar, Calif.

[21] Appl. No.: 09/172,924

[22] Filed: Oct. 14, 1998

[51] Int. Cl.[6] .................................................... A61N 1/08
[52] U.S. Cl. ............................................. 607/61; 128/903
[58] Field of Search ................................. 607/32, 33, 60, 607/61, 149; 600/391, 392; 128/703

[56] References Cited

U.S. PATENT DOCUMENTS

| | | | |
|---|---|---|---|
| 3,943,918 | 3/1976 | Lewis | 128/903 |
| 5,314,453 | 5/1994 | Jeutter | 607/61 |
| 5,511,553 | 4/1996 | Segalowitz | 128/903 |
| 5,578,065 | 11/1996 | Hattori et al. | 607/46 |

Primary Examiner—William E. Kamm
Assistant Examiner—George R. Evanisko
Attorney, Agent, or Firm—Bryant R. Gold

[57] ABSTRACT

A transcutaneous transmission patch transfers power and/or data to an implantable device implanted under a user's skin. The transcutaneous transmission patch is made of a flexible material with a top surface and a bottom surface. Located on or formed within the top surface is a pouch or cavity that houses electronic circuitry. The electronic circuitry typically includes a substrate on which an integrated circuit (IC) chip and a transmission coil are mounted. Alternatively, the transmission coil may be molded within the flexible material from which the pouch is made. The electronic circuitry is capable of transcutaneously transmitting power and/or data to a receiving coil in the implanted device. The electronic circuitry is powered by a battery or other power source which is also housed within the pouch or cavity or otherwise carried by the patch. The bottom surface of the transcutaneous transmission patch includes an adhesive layer that detachably secures the patch to a skin surface of the user. In one embodiment, the transcutaneous transmission patch is disposable. In another embodiment, select components of the transcutaneous transmission patch may be removed and reused.

18 Claims, 2 Drawing Sheets

TRANSCUTANEOUS TRANSMISSION PATCH

BACKGROUND OF THE INVENTION

The present invention relates to the transfer of electromagnetic energy between a transmission coil and a receiver coil, and more particularly, to an external transcutaneous transmission patch with a transmission coil, secured to the skin of a patient, transferring electromagnetic energy to an implanted device for transmission of power and/or data to the device and/or to a replenishable power source, e.g., a rechargeable battery, associated with the device.

Various types of medical devices such as cochlear implants, neural muscular stimulators, implantable pumps, and other implantable devices have been developed that are designed to be surgically inserted within a patient's body to carry out a medically related function for an extended period of time. Although a lead connected to the implanted device and extending outside the patient's body can be used to supply electrical power required to energize the device and/or control data, any lead that passes through the skin increases the risk of infection if left in place for more than a few days.

As an alternative to having a lead or wire pass through the skin of the patient, power and/or data can be supplied to an implanted medical device via an RF or electromagnetic link that couples power from an external (non-implanted) coil to an internal (implanted) coil. So long as a suitable link, e.g., an inductive link, is established between these two coils, which means some sort of external power source must be carried by or worn by the patient, power and/or data can be continuously supplied to the implanted medical device from the worn or carried external device, thereby allowing the implanted medical device to perform its intended function.

It is also known to power an implanted medical device with a battery that is housed internal to the implanted device. However, any battery used for extended periods of time will eventually need to be either recharged or replaced. Replacing an internally implanted battery subjects the patient to further surgery and thus is not desirable, at least not on a frequent basis.

Rather than replace an implanted battery, the battery can be recharged by transcutaneously coupling power from an external source to an implanted receiver that is connected to the battery. Although power can be coupled from an external source at radio frequencies using matching antennas, it is generally more efficient to employ an external transmission coil and an internal receiving coil which are inductively (electromagnetically) coupled to each other to transfer power at lower frequencies. In this approach, the external transmission coil is energized with alternating current (AC), producing a varying magnetic flux that passes through the patient's skin and induces a corresponding AC voltage in the internal receiving coil. The voltage induced in the receiving coil may then be rectified and used to power the implanted device and/or to charge a battery or other charge storage device (e.g., an ultracapacitor), which in turn powers the implanted device. For example, U.S. Pat. No. 4,082,097 discloses a system for charging a rechargeable battery in an implanted human tissue stimulator by means on an external power source.

Some implantable devices, such as neural or auditory stimulators, do not require internal batteries as a power source, but rather receive power directly via a transcutaneous coupling. Still other implantable devices, in addition to receiving power directly from an external power source, may also transmit information and data back to an external device relating to the status of the device and the signals it senses in the patient's body. See, e.g., U.S. Pat. No. 5,603,726, which describes an implantable cochlear stimulator powered by an external wearable system; and U.S. Pat. Nos. 5,324,316; 5,312,439; and 5,358,514; which describe a small implantable microstimulator. All of these patents—the '726 patent, the '316 patent, the '439 patent, and the '514 patent—are incorporated herein by reference.

When electromagnetic coupling is used to transfer power and/or data to an implanted device, alignment of the external device and the implanted device is critical for effective electromagnetic coupling. A common way of achieving the desired alignment between the external transmission coil and the implanted receiver coil is to employ a permanent magnet in both the headpiece which houses the external coil and the implanted device which houses the receiver coil. The magnetic attractive force associated with such magnets holds the external coil in close proximity to the receiver coil and provides the desired alignment between the coils so that inductive coupling may efficiently occur.

Another method of aligning an external unit with an implanted internal receiving device is shown in U.S. Pat. No. 5,545,191. In this patent, the external unit uses VELCRO® strips for attaching the external unit to the skin in a proper location for optimal electromagnetic coupling between the units.

As is known in the art, the efficiency with which electromagnetic power may be transcutaneously transferred between a transmission coil and a receiving coil, where one of the coils is implanted and the other is not, is a function of the alignment and distance between the coils. It is thus desirable to position the external device as close as possible to the implanted device.

Disadvantageously, existing external devices that supply electromagnetic power are bulky and large. These devices include a power source, control circuitry and a transmission coil. The power source (e.g., a battery and control circuitry) is usually attached to a person's belt or pocket. The transmission coil, which must be placed on the skin near the implanted device, is attached to the power source and control circuitry via an obtrusive, unsightly cable. See, e.g., U.S. Pat. No. 5,603,726.

In view of the above, it is evident that what is needed is a convenient unobtrusive external device that can transmit power and/or data transcutaneously to an implanted device, and wherein such external device is not only small and light weight, but is also readily attachable to the skin in close proximity to the implanted device.

SUMMARY OF THE INVENTION

The present invention advantageously addresses the above and other needs by providing an external transcutaneous transmission patch that includes all the necessary components for transmitting power and/or data to an implanted device. The implanted device may comprise a tissue stimulator, sensor, pump or any other implantable device that requires an electromagnetic link to be established therewith. The transcutaneous transmission patch is thin, light weight, and has an adhesive attached to one surface thereof to facilitate attachment of the patch to a patient's skin. That is, the patch includes a base having an adhesive backing (for attachment to the skin) and a closed pouch or cavity for housing the electronic components, e.g, a battery, a transmission coil, and electronic circuitry. Most or all of the electronic circuitry may be embodied in one or more integrated circuits.

The size of the transcutaneous transmission patch varies depending on the application with which the patch is used. Advantageously, it may be designed to receive any reasonably-sized battery, e.g., from a pair of AAA-sized batteries, to small disc-shaped watch/calculator/hearing-aid batteries.

The transcutaneous transmission patch is attached to a user's skin with an adhesive backing, similar to that used in a band-aid, or disposable transcutaneous electrical neuro stimulation (TENS) electrodes. In this way, the transcutaneous transmission patch can be removed and replaced, when required, with very little discomfort to the user.

In one embodiment, the transcutaneous transmission patch is fully disposable. That is, when the transcutaneous transmission patch needs to be replaced, the old transcutaneous transmission patch is removed and discarded, and a new transcutaneous transmission patch is attached to the patient's skin.

In other embodiments, some of the components of the transcutaneous transmission patch (i.e., electronic circuitry, transmission coil, and/or batteries) may be removed and reused, while others of the components are discarded after use. In such instance, the pouch or cavity of the patch may be divided into at least two sections, separating the disposable and non-disposable components, thereby allowing easy removal of the non-disposable parts, as well as convenient discarding of the disposable parts.

In use, the transcutaneous transmission patch is located as close as possible to the implanted device so as to provide the strongest signal coupling. In one embodiment, circuitry included with the patch responds to backtelemetry or reflected or other signals from the implanted circuitry, to provide a visual and/or audible signal when the best coil alignment has been achieved.

In some cases, it would be useful for the patient to be able to turn the system off and on without removing and discarding a partially depleted patch. Thus, another embodiment includes a simple on/off activation means, e.g. in the form of a press down button, temperature-sensitive activating switch, or the like.

It is thus a feature of the invention to provide a transcutaneous transmission patch that includes all of the necessary circuitry, including a power source (when a power source is needed), to couple power and control signals into an implant device.

It is another feature of the invention, in accordance with one embodiment thereof, to provide such a transcutaneous transmission patch that is fully or partially disposable.

It is yet an additional feature of the invention to provide such a transmission patch that readily attaches to the skin of a patient, using a suitable adhesive spread on one surface, much like disposable/reusable skin electrodes of the type commonly used with TENS units, thereby facilitating the patch's positioning and adherence to the skin of a patient.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Advantageously, the transcutaneous transmission patch of the present invention provides a self-contained device including a power source, electronic control circuitry, and transmission coil that is compatible with many types of implanted devices, e.g., microstimulators, tissue stimulators, sensors, pumps, and the like. The transcutaneous transmission patch is self-adhering to the skin, easy to apply and remove, unobtrusive, can be made in variety of colors or shapes, is disposable and inexpensive. Components of the transcutaneous transmission patch may also be recycled and reused. In one embodiment, alignment aids, e.g., an audible alarm (beeping sound) or visual signal (light emitting diode, or LED), or other perceivable signals, are included as part of the patch to signal when proper alignment with an implant device has been achieved. In some embodiments, an on/off switch is included.

Figure 1:
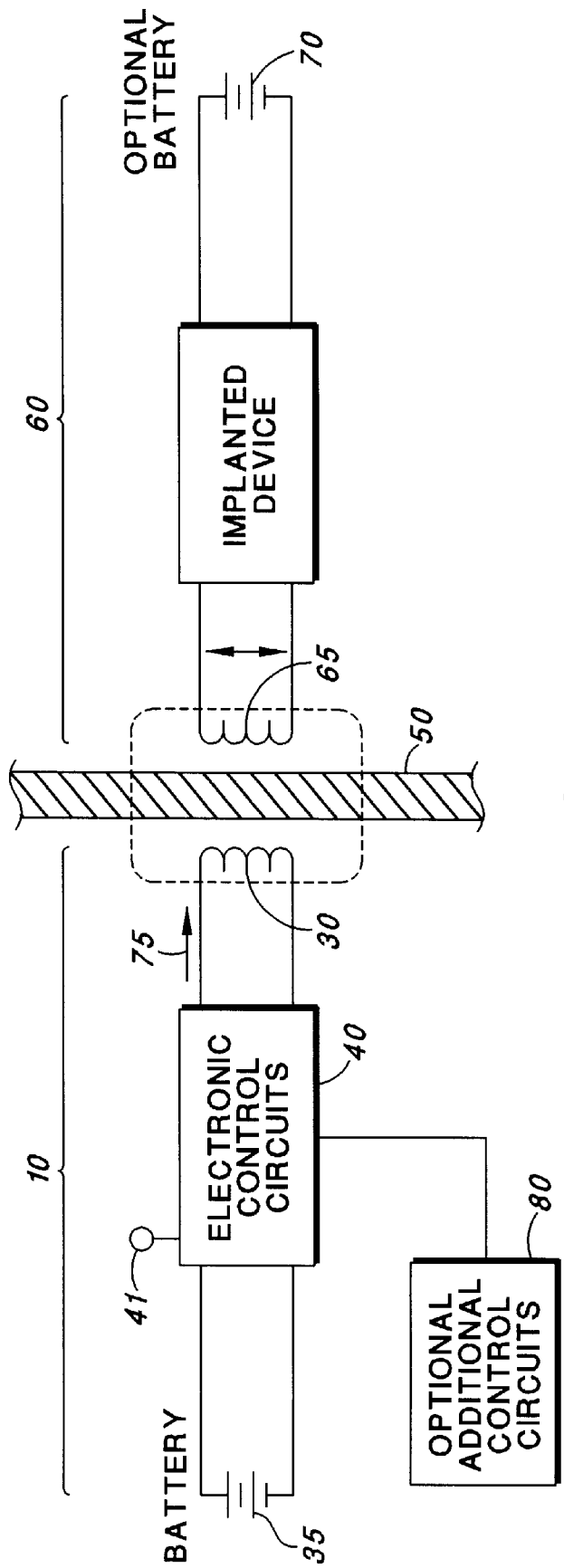
FIG. 1 is a block/schematic view of the present invention.

Referring first to FIG. 1, there is shown a schematic diagram of an externally wearable transcutaneous transmission patch 10 made in accordance with the present invention for use with an implantable device 60 (such as an implanted neural stimulator or microstimulator or sensor). The transcutaneous transmission patch 10 transmits a modulated signal 75 from an external transmission coil 30, through the skin layer 50, to an internal receiving coil 65 of the implanted device 60. The modulated signal 75 is controlled by an integrated circuit chip 40 powered by a battery 35, or other power source (e.g., a supercapacitor, ultracapacitor, or other energy-storage device). Circuitry within the implanted stimulator 60 demodulates the signal to obtain data, and/or rectifies the signal to obtain power, as is known in the art. The recovered data may be used to control the operation of the implanted stimulator. Optionally, the implanted device 60 may also contain a battery 70 or other power source, e.g., an ultracapacitor. The battery or other power source 70 is preferably of the rechargeable type, in which case, the transcutaneous transmission patch 10 is used to supply the power for recharging the battery 70 or other power source with power derived from the modulated signal 75. Hence, the external transcutaneous transmission patch 10, without the need for any through-the-skin connectors, and without the need for any complex implanted multiplexing schemes or circuitry, is able to selectively control and/or power the implanted stimulator 60.

In some embodiments, the implanted device includes backtelemetry circuitry that allows the transmission of data and signals from the implanted system 60 to the external device 10. Such backtelemetry data may include, e.g., an indication of the voltage level obtained by rectifying and filtering the inductively-coupled carrier signal received from the external patch 10. Such voltage will be at a peak (maximum) value when the implant coil 65 and external coil 30 are properly aligned. Thus, such signal may be used as a feedback signal to trigger circuitry within the transmission patch whenever proper alignment and/or improper alignment exists. The external transmission patch, in such embodiments, may include a suitable audible and/or visual indicator 41 that alerts the patient (or other person who is attaching the transmission patch 10 to the skin of the patient) when proper coil alignment has been achieved.

It should be noted that other types of feedback signals could also be used to provide the needed alignment information for such optional alignment-indicating circuitry, all of which could be used with the invention. For example, circuitry within the patch 10 may monitor, on a sampled basis, the reflected impedance as seen by the coil 30. Such impedance, depending upon how it is monitored, will reach either a maximum or a minimum when proper alignment is achieved. Still by way of example, circuitry within the patch 10 could acoustically monitor reflected signals from devices implanted near the skin in order to locate such devices, much like a stud finder finds studs behind a wall.

Figure 2:
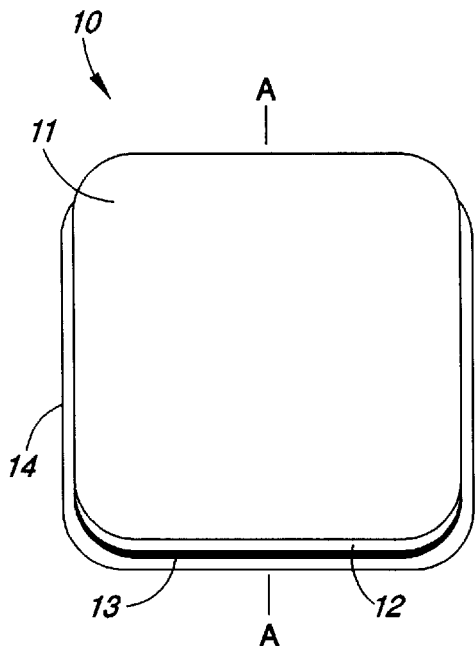
FIG. 2 is a top view of the present invention.

FIG. 2 shows a top view of the transcutaneous transmission patch 10, within which embedded and/or removable electronic components, e.g., batteries, integrated circuits, and receiver coil, may be housed in a flexible material 12 with a top surface 11 and an adhesive base 13, upon a removable backing 14. When the patch 10 is ready to be adhered to the skin of the patient, removable backing 14 is simply peeled away from the adhesive base 13, and the patch is placed on the skin at the desired location. As explained above, the transcutaneous transmission patch 10 is used to supply power and/or data to an implanted device 60, such as a stimulator, pump or other device that requires power and/or data to be coupled thereto transcutaneously.

Figure 3:
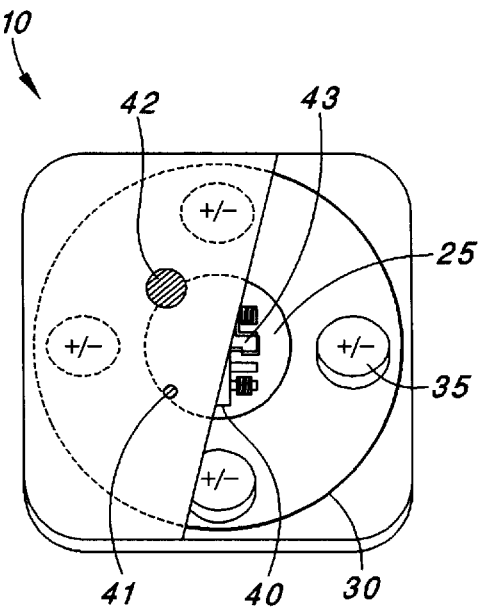
FIG. 3 is a top view similar to FIG. 1 with the top layer partially removed to show more detail of the interior components of one embodiment.

FIG. 3 similarly shows a top view of the transcutaneous transmission patch 10, but with part of the top surface peeled back to show some detail associated with the interior components. Such components include, e.g., a set of batteries 35, an electronic substrate 25 with integrated circuit (IC) chip 40 and other electronic componentry 43, and a transmission coil 30. FIG. 3 also shows optional surface components including a visual alignment indicator 41 (such as an LED or light) and an on/off switch 42 (such as a depressable button). Because the costs associated with the manufacture of IC chips and coils have reduced in recent years, one embodiment of the invention contemplates that the entire transcutaneous transmission patch 10 may be disposable. Alternatively, all or part of the transcutaneous transmission patch 10 may be reused, as will be discussed later.

Figure 4:
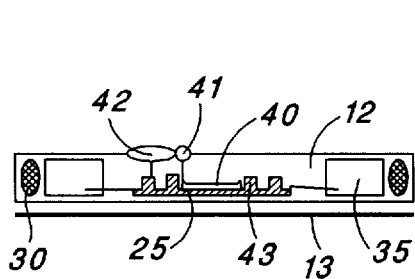
FIG. 4 is a cross-sectional view taken along A—A of FIG. 2 showing one embodiment of the present invention in use with an implanted stimulator.
Figure 6:
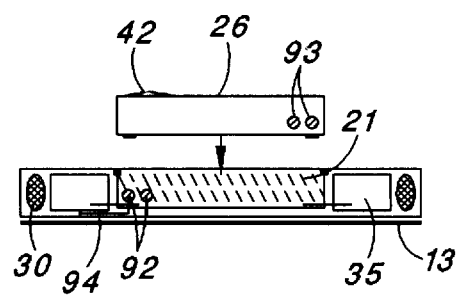
FIG. 6 is a cross-sectional view taken along A—A of FIG. 2 of another embodiment of the invention, illustrating the manner in which a button-module, containing, e.g., electrical circuitry, may be detachably snapped into a cavity located within a flexible substrate, the flexible substrate having a coil and batteries embedded therein.
Figure 5:
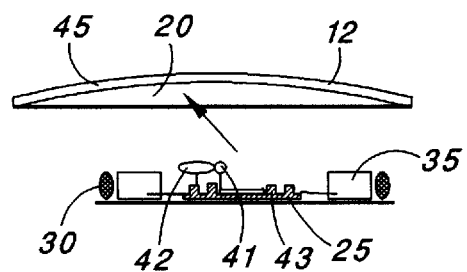
FIG. 5 is a cross-sectional view taken along A—A of FIG. 2 showing an alternate embodiment of the present invention in use with an implanted stimulator.

FIGS. 4–6 illustrate cross sectional views of 3 embodiments of the patch 10 taken along the line A—A of FIG. 2. FIG. 4 illustrates a fully disposable embodiment. As seen in FIG. 4, all of the electronic circuitry is embedded in a flexible base material 12 (hereafter referred to as the patch base material). The electronic circuitry includes a substrate 25 supporting Integrated Circuit (IC) chip 40 and other electronic components 43, a transmission coil 30, and batteries (or other power units) 35. In some embodiments of the invention, an alignment indicator 41 may be mounted on the IC chip 40 to provide a signal that indicates when proper coil alignment has been achieved. Likewise, in some embodiments of the invention, an on/off switch 42 may be added into the circuitry so that a single patch can be intermittently used, before being discarded. In a fully disposable embodiment, once the batteries (or other power units) 35 in the transcutaneous transmission patch 10 are discharged, the patch 10 is removed and a new transcutaneous transmission patch 10 is applied.

Although the batteries illustrated in FIG. 3 are shown as being button shaped batteries of the type commonly used in watches, calculators, and hearing aids, it is to be understood that other types or shapes of batteries may also be employed, e.g., cylindrical AAA type batteries. It is also to be understood that other types of power storage devices, e.g., an ultracapacitor(s), may also be used within the patch 10 and/or the implant device 60, to provide needed operating power. Ultracapacitors (which are also commonly referred to as supercapacitors), as is known in the art, have a very high energy density, which means they are able to store large amounts of energy in a small volume or space. Unlike batteries, which produce energy electrochemically, a capacitor only stores energy that it receives from an external source. Nevertheless, once charged (i.e., once an ultracapacitor has energy stored therein from an external source), an ultracapacitor may provide a very usable power source, which can be readily recharged, as frequently as required, in which case it would be advantageous to include the reusable power source within a removable substrate.

In one embodiment, illustrated in FIG. 5, the compartment 20 of the transcutaneous transmission patch 10 comprises a pouch having an opening 45, e.g., along one edge thereof, allowing access for the insertion of components. The contents of the pouch 20 (substrate 25 with the transmission coil 30, batteries 35 and IC chip 40) are inserted through the opening 45. Such opening 45 may be sealed (closed) or unsealed (open) using a zip-lock or adhesive mechanism as is known in the art. In another embodiment, certain components could be left off of the removable substrate 25, and would be embedded within the patch 10 to be part of the disposable component group, e.g. transmission coil 30 and/or batteries (or other power units) 35. Thus, in FIG. 5, there is a disposable portion including at least the patch itself, and a re-usable portion that contains some or all of the electronic components for transmitting power and/or data to the implanted device 60.

In another embodiment, the compartment 20 of the transcutaneous transmission patch 10 comprises a cavity having an opening at its top into which the components of the transmission patch may be detachably inserted, e.g., snapped into position within the cavity, as shown in FIG. 6, discussed in more detail below. It may be advantageous to encase the reusable electronic circuitry, e.g. IC 40, into a button module 26 that can be snapped into the cavity 21 formed in the patch base 12.

For embodiments of the invention which reuse some of the components (as opposed to disposing of the entire patch, including all of its components), many different combinations of reusable verses disposable components are envisioned. For example, just the batteries 35 may be reused (snapped into cavity 21) with chip 40 and other components embedded in the patch 10. Alternatively, the transmission coil 30 and IC chip 40 may be reused, and the patch substrate 25 and batteries 35 may be disposed. Still further, the patch base material 12 may have a transmission coil 30 embedded therein, and the patch base/coil may be disposable. One or more batteries 35 may also be housed on substrate 25 to be selectively removable and disposable therefrom, separately from the disposable patch. Thus, the patch may be disposed of with daily usage, while the battery may be used for weeks with the removable substrate and replaced after depletion. Thus, it is seen that a wide variety of combinations of disposable and reusable components may be used with the invention. In this way, the patient can reuse the more expensive items (e.g. electronics substrate 25 with batteries 35) and replace the inexpensive items (e.g. patch with coil 30). Such alternative design options are all within the scope of this invention and are guided by cost and usage requirements.

Referring again to FIG. 4, it is seen that the transcutaneous transmission patch 10 is designed to be secured to the skin of a patient 50. The patch 10 includes an adhesive base 13. Preferably, the patch 10 is constructed of flexible non-rigid materials in order to conform to the contour of the portion of the user's skin 50 to which the patch 10 is attached and can be made in a variety of shapes and colors (like skin color or designer colors). The adhesive base 13 is similar in construction to a band aid or TENS electrode, using a breathable, conformable, elastic adhesive bandaging material as is known in the art With reference to the embodiment shown in FIG. 6, the cavity 21 includes a plurality of coil terminals 92 formed in a side wall thereof. Such terminals are electrically connected, through wires 94 that pass through the patch base material 12, to the embedded coil 30, and/or other disposable circuit components. The coil 30 typically comprises multiple turns of suitable-sized fine wire.

The button module 26, which is adapted to snap into the cavity 21, includes suitable electrical contact points 93 along one of its edges. These contact points are electrically connected to the electrical/electronic circuitry 43 included within the module 26. When the module 26 is snapped into the cavity 21, a lip or ridge around the periphery of the cavity 21 may be used to help seal the interface between the removable module 26 and cavity 21. Further, when the module 26 is snapped into the cavity 21, the electrical contact points 93 are oriented so as to make electrical contact with the terminals 92 of the patch base material 12. As needed, the module 26 may be physically keyed to assure that the desired electrical contact is established. Alternatively, the contact points 93 may comprise annular rings, and the terminals 92 in the wall of the cavity 21 may be vertically spaced apart, so that regardless of the orientation of the module 26 as it is snapped into the cavity 21, the desired electrical connection is made, thereby electrically connecting the coil 30 and/or other embedded components to the electrical circuits within the module 26.

As indicated previously, some embodiments of the invention include an indicator 41 that provides a visual and/or audible indication when the proper alignment has been achieved with the implanted receiving coil. For such embodiments, the user of the device may leave the removable backing 13 in place while sliding (or otherwise moving and repositioning) the patch over the skin in order to find the proper location for affixing the patch. Once such location is found, then the removable backing 14 may be peeled away, and the patch 10 may be readily adhered to the found location.

It is contemplated that for some embodiments of the invention, the electronic circuitry 43 will include selective switch means for selectively enabling the visual/audible indicator 41. For example, a magnetically activated switch may be included in such circuitry so that when a small permanent magnet is placed over the area of the patch 10 under which the electronic circuitry 43 is located, the switch is activated to enable the visual/audible indicator 41. Once the patch has been affixed to the skin, such magnet can be removed, disabling the visual/audible indicator 41, thereby conserving power. Other types of enabling/disabling switches could, of course, also be used for this purpose, or other purposes.

For embodiments that do not include a user on/off switch (e.g. a depressable button or touch/heat sensitive surface) some means for turning the power on when a patch is being used is preferred so that stored transmission patches containing individual power sources would not be depleted before use. Hence, a patch 10 may include means for automatic activation as soon as the peel back surface 14 is removed from the adhesive 13. Likewise, the patch could be activated only when alignment with the implant is detected, a magnetic interface with the implant is detected, or proximity to the skin of the user is detected through a built-in temperature sensor. Thus, it is seen that any means for automatically or selectively activating a power source as is known in the art would be within the scope of the invention for turning the patch on or off.

In embodiments where the transmission patch is used not only for powering or recharging the implant, but also for controlling the operation of the implant, stored control information is required in the electronic circuitry of the patch for individual patients. Thus the transmission patch would also be programmable. The patches could be pre-programmed with stored information, or the patient may have a patch programmer that stores information for that patient to download software control information to each patch before use. For example, a neural stimulator may have many parameters for stimulating that are programmable for a patient including pulse width, frequency, and amplitude. The patient may use a patch programmer, that stores the patient's selected values for those and other parameters, to set the control output of the patch. Likewise, the patient could use the programmer to vary patch settings as needed. This approach would also be valuable in setting patch outputs for controlling the operation of implantable pumps and sensors.

From the above, it is thus seen that the present invention provides a self-contained device including a power source, electronic control circuitry, and transmission coil that is compatible with many types of implanted devices. The transcutaneous transmission patch is self-adhering to the skin, easy to apply and remove, unobtrusive, can be made in variety of colors or shapes, is disposable and is inexpensive. Components of the transcutaneous transmission patch may also be recycled and reused.

While the invention herein disclosed has been described by means of specific embodiments and applications thereof, numerous modifications and variations could be made thereto by those skilled in the art without departing from the scope of the invention set forth in the claims.

What is claimed is:

1. A method for transmitting signals through the skin of a user to a receiving coil of an implantable unit, comprising the steps of:

(a) providing a flexible transcutaneous transmission patch having a pouch formed therein wherein electronics and a power source for transmitting signals to the implantable unit are removably carried, the transcutaneous transmission patch having means for adhesively securing it to a surface of the user's skin; and (b) detachably securing the transcutaneous transmission patch to the user's skin at a position that allows signals to be coupled from the electronics to the implantable unit.

2. The method of claim 1 further comprising inserting selected components removed from the transcutaneous transmission patch into a pouch of a new transcutaneous transmission patch, and detachably securing the new transcutaneous transmission patch to the skin surface of a user, whereby selected components are reused in the new transcutaneous transmission patch.

3. A transcutaneous transmission patch for transmitting power and data signals to an implantable medical device comprising:
- a flexible substrate comprising a flexible material having a top surface and a bottom surface and a pouch formed between the top surface and bottom surface;
- means for opening and closing the pouch;
- means for adhesively securing the bottom surface of the flexible substrate to a skin surface;
- electronic circuitry carried by the flexible substrate, the electronic circuitry including means for generating power and data signals for the implantable medical device;
- a power source carried by the flexible substrate and connected to the electronic circuitry for supplying operating power to the electronic circuitry; and
- means for transmitting the power and data signals generated by the electronic circuitry through body tissue to the implantable medical device;
- wherein at least one of the means for transmitting, electronic circuitry, and power source are removably carried in the pouch.

4. The transcutaneous transmission patch of claim 3 wherein the power source comprises at least one energy storage device.

5. The transcutaneous transmission patch of claim 4 wherein the at least one energy storage device comprises a battery.

6. The transcutaneous transmission patch of claim 4 wherein the at least one energy storage device comprises a capacitor.

7. The transcutaneous transmission patch of claim 3 wherein the electronic circuitry includes an integrated circuit (IC) chip.

8. The transcutaneous transmission patch of claim 3 wherein the means for transmitting the power and data signals comprises a transmission coil connected to the electronic circuitry and carried by the flexible substrate.

9. The transcutaneous transmission patch of claim 8 further including means for selectively activating the electronic circuitry carried by the flexible substrate.

10. The transcutaneous transmission patch of claim 9 wherein the means for activating the electronic circuitry comprises an on/off switch that may be selectively activated to turn the means for generating the power and data signals on and off.

11. The transcutaneous transmission patch of claim 9 wherein the means for activating the electronic circuitry comprises a switch that is automatically activated when the flexible substrate is adhesively secured to the skin surface.

12. The transcutaneous transmission patch of claim 8 wherein the electronic circuitry includes sensor means for sensing when the transmission coil is in proper alignment with the implantable medical device.

13. A transcutaneous transmission patch for transmitting power and data signals to an implantable medical device comprising:
- a flexible substrate comprising a flexible material having a top surface and a bottom surface;
- a cavity formed in the top surface;
- a module sized for detachable insertion into the cavity;
- means for adhesively securing the bottom surface of the flexible substrate to a skin surface;
- electronic circuitry including means for generating power and data signals for the implantable medical device;
- a power source connected to the electronic circuitry for supplying operating power to the electronic circuitry; and
- means for transmitting the power and data signals generated by the electronic circuitry into body tissue to the implantable medical device;
- wherein at least one of the means for transmitting, electronic circuitry, and power source, are carried within the module and can thus be removed from the cavity by removing the module from the cavity; and
- any of the means for transmitting, electronic circuitry, and power source not carried within the module are embedded between the top and bottom surface of the flexible substrate.

14. The transcutaneous transmission patch of claim 13 wherein the power supply is carried within the module, and wherein the module includes means for removing the power supply carried therein, whereby a depleted power supply may be removed from the module and replaced with a new power supply.

15. The transcutaneous transmission patch of claim 13 further including means for selectively activating the electronic circuitry carried on the flexible substrate.

16. The transcutaneous transmission patch of claim 13 wherein the electronic circuitry includes sensor means for sensing when the transmission coil is in proper alignment with the implantable medical device.

17. A transcutaneous transmission patch comprising:
- a flexible substrate, wherein the flexible substrate includes an openable and sealable pouch;
- means for adhesively securing the flexible substrate to a skin surface; and
- electronic componentry including a transmission coil, a power source, and electronic circuitry for coupling and modulating power from the power source to the transmission coil and transmitting signals through the flexible substrate into a body;
- wherein at least one of the transmission coil, power source and electronic circuitry is carried within the openable and sealable pouch and can be removed therefrom and replaced when necessary; and
- wherein the electronic componentry not carried within the openable and sealable pouch is embedded within the flexible substrate.

18. A transcutaneous transmission patch for transmitting signals to an implantable medical device comprising:
- a flexible substrate;
- means for adhesively securing the flexible substrate to a skin surface;
- electronic circuitry carried by the substrate, the electronic circuitry including means for generating power and data signals;
- a power source carried by the substrate and connected to the electronic circuitry for supplying operating power to the electronic circuitry, wherein the power source comprises a capacitor wherein energy is stored; and
- means for transmitting the power and data signals generated by the electronic circuitry into body tissue below the skin surface to the implantable medical device.

* * * * *